United States Patent [19]
Fyfe

[11] Patent Number: 5,955,667
[45] Date of Patent: Sep. 21, 1999

[54] MOTION ANALYSIS SYSTEM

[75] Inventor: Kenneth Richard Fyfe, Fort Saskatchewan, Canada

[73] Assignee: Governors of the University of Alberta, Edmonton, Canada

[21] Appl. No.: 08/949,472

[22] Filed: Oct. 14, 1997

Related U.S. Application Data

[60] Provisional application No. 60/028,367, Oct. 11, 1996.

[51] Int. Cl.$^6$ .................................................. G01P 15/08
[52] U.S. Cl. ............................ 73/490; 73/865.4; 73/510; 702/160
[58] Field of Search ............................ 73/490, 492, 489, 73/865.4, 510; 235/105; 377/24.2; 340/323 R; 482/3, 7, 8, 74; 702/141, 160, 166

[56] References Cited

U.S. PATENT DOCUMENTS

| | | | |
|---|---|---|---|
| 4,371,945 | 2/1983 | Karr et al | 340/323 R |
| 4,736,312 | 4/1988 | Dassler et al. | 340/323 R |
| 5,097,706 | 3/1992 | Le Nouvel et al. | 73/865.4 |
| 5,583,776 | 12/1996 | Levi et al. | 364/450 |
| 5,724,265 | 3/1998 | Hutchings | 364/565 |

FOREIGN PATENT DOCUMENTS

| | | |
|---|---|---|
| 4222373 | 1/1994 | Germany . |
| 862074 | 10/1981 | Russian Federation . |
| 885897 | 11/1981 | Russian Federation . |

OTHER PUBLICATIONS

Estimation of Speed & Incline of Walking Using Neural Networks Aminian et al. IEEE Transactions on Instrumentation & Measurement vol. 44 No. 3 Jun. 95.

*Primary Examiner*—Michael Brock
*Assistant Examiner*—Helen C. Kwok
*Attorney, Agent, or Firm*—C. A. Rowley

[57] ABSTRACT

A device comprised of at least a pair of accelerometers and a tilt sensor mounted in fixed relation to a datum defining plane (sole of a shoe) maybe used for extracting kinematic variables including linear and rotational acceleration, velocity and position. These variables may be resolved into a selected direction thereby permitting both relative and absolute kinematic quantities to be determined. The acceleration is determined using a small cluster of two mutually perpendicular accelerometers mounted on a shoe. Angular orientation of the foot may be determined by double integration of the foot's angular acceleration (which requires a third accelerometer substantially parallel to one of the two orthogonal accelerometers). The two orthogonal accelerations are then resolved into a net horizontal acceleration or other selected direction which may be integrated to find the foot velocity in the selected direction. The average of the foot velocity corresponds to the subject's gait speed.

20 Claims, 18 Drawing Sheets

Tangential
Acceleration

Normal
Acceleration

Foot Tilt
Angle

Horizontal
Acceleration

Horizontal
Foot Velocity

Mean Speed
of Travel

MOTION ANALYSIS SYSTEM

This Application claims benefit of Provisional Appln. 60/028,367 filed Oct. 11, 1996.

FIELD OF THE INVENTION

The invention relates to a method and apparatus for measuring acceleration, velocity and position of gait based on foot movement analysis.

BACKGROUND OF THE INVENTION

The measurement and characterization of gait (i.e. human or animal) is performed by a wide range of methods. At one end of the scale is the measurement and analysis possibilities found in a well equipped bio-mechanical lab. The equipment in these labs typically includes automated 3D optical measurement systems, force plates and physiological output indicators. The output from these transducers are fed into a central computer that enables a wide range of analysis and display possibilities. At the other end of the spectrum is the simplified analysis performed with a ruler, stopwatch and trained clinical observations.

The reasons determining gait kinematic properties (such as acceleration, velocity and position) range from: (i) personal interest, (ii) training and performance considerations of the serious athlete, (iii) rehabilitation of the disabled or (iv) for the design and analysis of footwear.

From an athletic point of view, runners, joggers and walkers often like to know how far they have journeyed and how fast they have traveled, but have had only limited cumbersome ways to measure distance and speed. Distance can be measured after the fact with a calibrated bicycle or automobile or by traveling on a known premeasured route. For determining one's speed, a simple approach is to travel a known, fixed distance on a track or road and then record the length of time required to cover the distance. This method suffers from several limitations including (i) limited walking/running routes, (ii) speed indication at measured intervals only and (iii) only an average velocity is determined over the given distance.

There are a number of portable pedometers that attempt to tackle the problem of measuring both distance and velocity. However, they have failed to gain wide spread use, because these devices are essentially limited to stride counting. Distance and speed can only be estimated if stride length consistency is assumed. This approach is inaccurate because an individual's stride length changes considerably from day to day or even within one session due to changes in terrain, fatigue, interval training, or other factors.

U.S. Pat. No. 3,355,942 discloses a pedometer that counts strides based on compression cycles in a bellows under the heel and then estimates distance based on average stride length. The invention described in U.S. Pat. No. 4,741,001 uses a spirit-biased pendulum to count strides. The pedometer disclosed in U.S. Pat. No. 4,649,552 uses a step sensor sealed into an insole to count strides. The pedometer of U.S. Pat. No. 4,651,446 counts strides by detecting flexion of the instep. Other counting pedometers include those under U.S. Pat. Nos. 5,117,444, 5,065,414, 4,855,942, 4,510,704, 4,460,823, 4,371,945, 4,322,609, 4,053,755, 3,818,194 and 3,635,399.

The majority of the patented pedometers are simply different methods of stride counting and do not address the problem of varying stride length. However, a pedometer listed under U.S. Pat. No. 4,371,945 uses ultrasonic emitters and sensors on alternate legs to measure the maximum distance between legs during each stride. While this is a significant improvement, this is only suitable for simple, low-speed gait patterns (no flight stage) and requires two sets of transducers; one on each leg.

The broad concept of using accelerometers for determining the velocity and distance traveled, for example by athletes, is described in German Patent 4,222,373. This patent describes the use of an accelerometer and integration to determine velocity and route or position. This device apparently processes acceleration data continuously and thus has an accumulated error from drift so that in very short period of time, the resulting data contains significant inaccuracies. The inventor indicates that this device is useful for skiers, surfers, sailors, cyclists, etc. and thus is not related to a striding device or for measuring the kinematics of striding and would not be effective for that purpose.

The Russian Patents 862074 and 885879 both by Volkov describe the attempts to overcome accumulated error in acceleration measuring devices by using a bar generator in combination with a summator and integrator. This described device does not make use of updated reference points and is thus also prone to accumulated drift.

A paper entitled "Estimation of Speed and Inclination of Walking Using Neural Networks" by Aminian et al., Published in the *IEEE, Transactions on Instrumentations and Measurements;* Volume 44 #3, June 1995, describes a portable data logger designed to record body accelerations during walking and uses three orthogonal accelerometers placed on the waistbelt to measure forward, vertical and heel acceleration. By means of neural networks, it correlates the recorded signals to the desired gait velocity and angle of incline. The generality of this method is questionable and no other gait information is produced.

BRIEF DESCRIPTION OF THE PRESENT INVENTION

The purpose of the device described herein is to provide a means to measure and display several human gait parameters (that may include instantaneous and average accelerations and velocities as well as total distance traveled) by means of a simple, low-cost, portable transducer that can accommodate a wide variety of gaits and varying stride length.

The present invention measures various parameters about each individual stride rather than assuming a given fixed length. With suitable signal processing, it can accurately determine velocity and distance traveled. The present invention can be modified to give many other useful indicators to the user such as pronation angles and impact forces. Because it is based on acceleration measurements and analysis, it inherently contains data that correlate directly to impact forces. When integrated, the acceleration data yields both instantaneous and average velocity. A second integration of these signals yields distance information such as total distance traveled or stride length. Other relevant pieces of information include stride rate and peak heel velocity. The invention also has the potential to measure biomechanic parameters such as degree of pronation and gait sway.

In broad terms, the present invention relates to a method of determining gait kinematics comprised during each stride defining a datum plane, determining angles between a pair of mutually perpendicular accelerometers to said datum plane, said pair of mutually perpendicular accelerometers adapted to measure acceleration in two mutually perpendicular directions in a plane of motion substantially perpendicular to said datum plane, measuring acceleration in said plane of motion in said two directions and converting said accelerations to provide acceleration in a selected direction.

Preferably said selected direction is parallel to the datum plane and said plane of motion.

Preferably said method further comprises integrating said acceleration in said selected direction to define velocity in said selected direction.

Preferably said datum plane is defined by the position of a sole plane when said sole plane is at rest on a surface in a stance phase of said gait and wherein said pair of mutually perpendicular accelerometers are positioned in fixed relationship to said sole plane.

Preferably said determining angles of a pair of mutually perpendicular accelerometers is based on measurements of a pair spaced parallel accelerometers positioned at a selected angle to said sole.

Preferably further comprising integrating said velocity to define distance in said selected direction.

Preferably said velocity is averaged over a plurality of strides to provide average velocity.

Broadly the present invention also relates to a device for measuring stride kinematics comprising means for mounting pair(s) of mutually perpendicular accelerometers in a fixed relationship to a datum plane defining surface and adapted to measure acceleration in said two mutually perpendicular directions, means for determining angular orientation of said accelerometers to a datum plane defined by a plane occupied by said datum plane defining surface when said plane defining surface is in a stationary position in a stance phase of said stride and means for determining acceleration in a selected direction based on measurements of acceleration by said mutually perpendicular accelerometers and said determined angular orientation of said accelerometers to said datum plane.

Preferably said means to determine angular orientation of said accelerometers to said datum plane comprises of a pair of spaced substantially parallel accelerometers mounted in fixed relation to said datum plane defining surface and means for calculating angular orientation based on differences in accelerations measured by said pair of spaced substantially parallel accelerometers.

Preferably said device further comprises means for converting acceleration in said selected direction to velocity in said selected direction be means of integration.

Preferably said device further comprises means to convert said acceleration in said selected direction to distance in said selected direction.

BRIEF DESCRIPTION OF THE DRAWINGS

Further features, objects and advantages will be evident from the following detailed description of the preferred embodiments of the present invention taken in conjunction with the accompanying drawings in which;

FIG. 3A is a view similar to FIG. 6 but showing a preferred arrangement.

FIGS. 4Aa, 4Ab and 4Ac are plots of upper tangential acceleration, lower tangential acceleration and normal acceleration respectively versus time.

FIG. 5A is a plot of foot acceleration during a single step.

FIGS. 6Aa, 6Ab and 6Ac are plots of angular acceleration, angular velocity and angular position respectively versus time.

DESCRIPTION OF THE PREFERRED EMBODIMENTS

Figure 1:
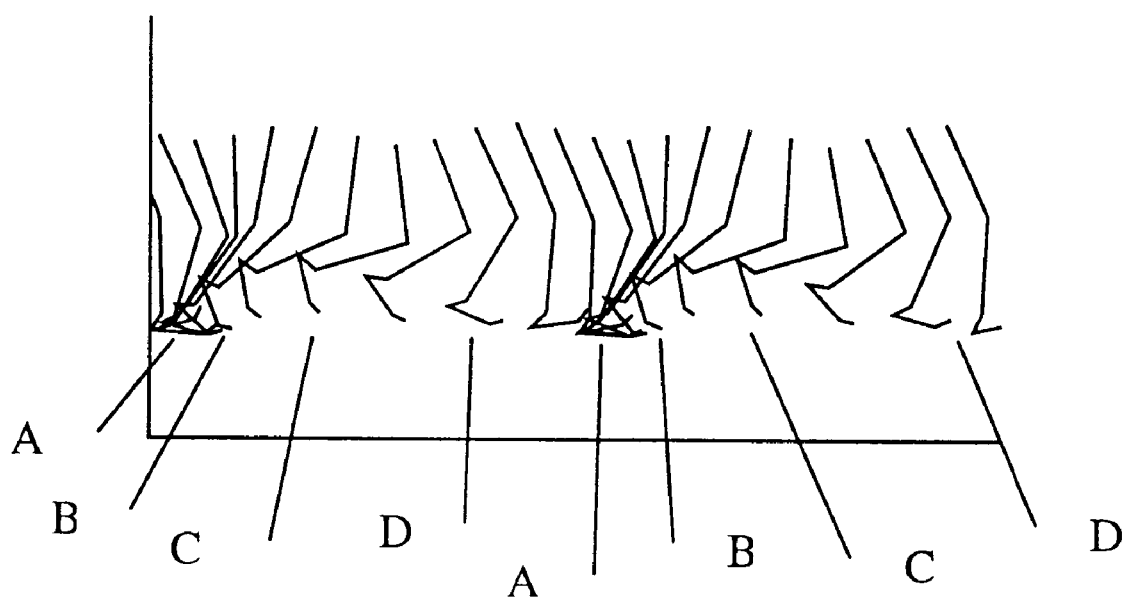
FIG. 1 is a schematic illustration of leg movement during walking or running.

FIG. 1 shows various stages of gait in a runner (3 complete gait cycles are shown). The foot plants on the ground or supporting surface and comes to a complete rest in what is known as the stance phase of gait cycle as indicated at Points A in FIG. 1. The foot then begins to accelerate as indicated at B in FIG. 1 as the toe prepares to take off. The swing phase indicated at C follows as the leg passes through the air. Following this, the foot decelerates as it prepares to strike the ground as indicated at D and then repeats the cycle. These accelerations, decelerations and stoppings are utilized in the present invention to determine gait kinematics as will be described below.

The fact that the foot plants and it becomes at rest or stationary during the stance phase A is used to provide a datum position to define a datum plane for each stride of the gait thereby eliminating accumulated error that would be adherent in the process if it wasn't iterated commencing at each stance phase A.

Figure 6:
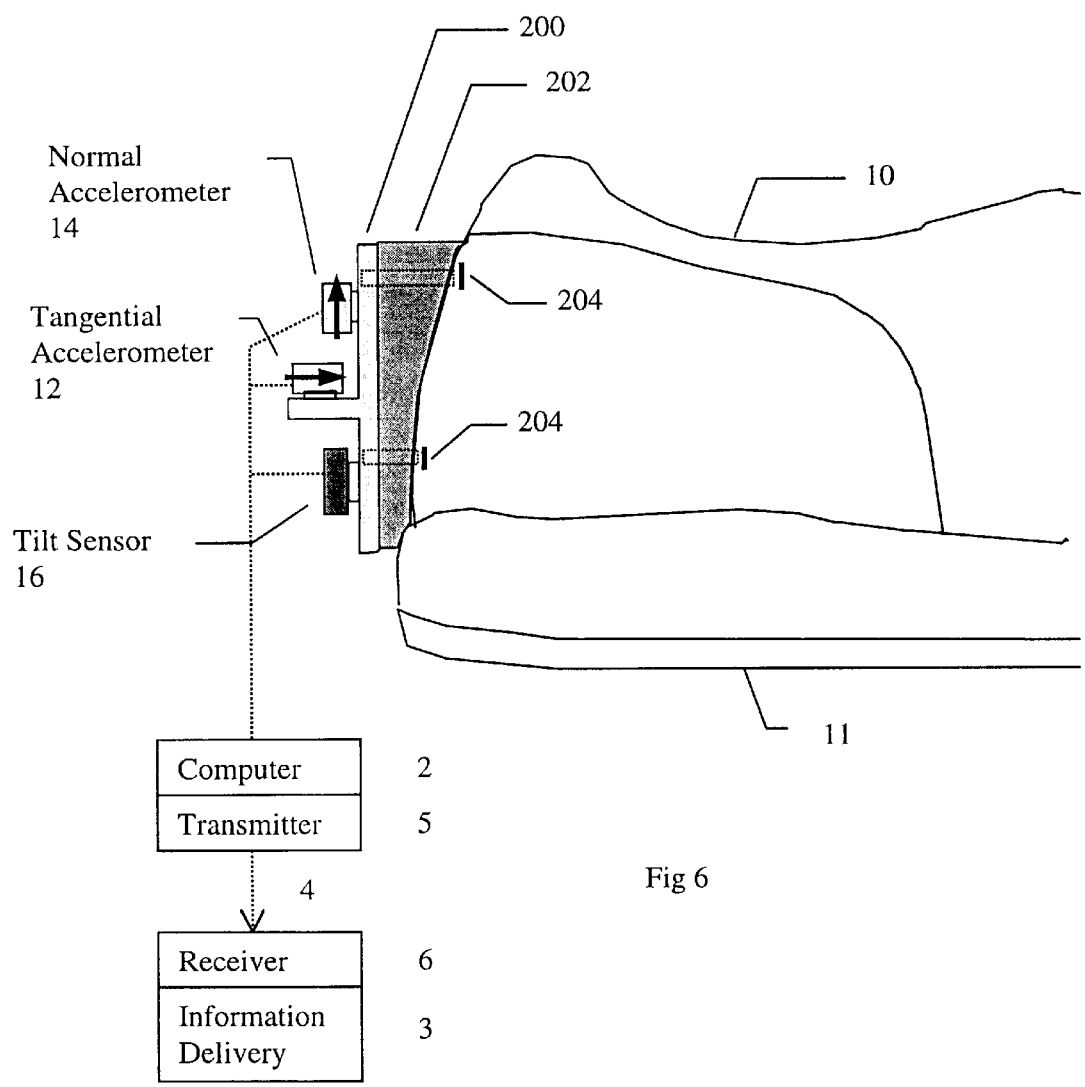
FIG. 6 is a more detailed illustration of the accelerometers mounted on the shoe, and schematically illustrating their connection to a computer.

The information to permit gait kinematic investigations is obtained via suitable sensors preferably acceleration sensors (accelerometers) 12 and 14 and a tilt sensor 16 and this information is fed to a suitable computer 2 that performs calculations transferred from the data from the accelerometers into the information format for delivery system 3 and displayed in the selected format (see FIG. 6).

The information may be transferred directly as represented by the arrow 4 or transferred by a transmitter 5 and then picked up by a receiver 6 in the display unit.

Figure 2:
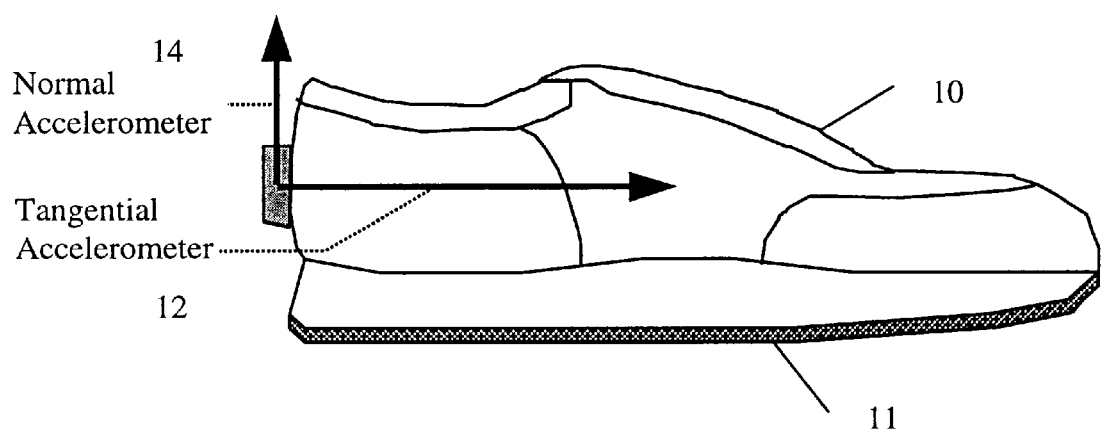
FIG. 2 shows a shoe with accelerometers mounted thereon.

Two mutually perpendicular accelerometers 12 and 14 and a tilt sensor 16 (see FIG. 6) are mounted on the heel counter of a shoe 10 and thus in fixed position relative to a datum plane defining surface (sole) 11 of the shoe 10 as will be described below. The accelerometers are preferably (but not necessarily) orthogonally mounted as shown such that in the neutral standing position one is oriented vertically and one horizontally (FIG. 2). The vertical accelerometer 14 is referred to as the normal accelerometer and the horizontal accelerometer 12 is referred to as the tangential accelerometer. These accelerometers measure the accelerations of the heel as the leg traverses through the sagittal plane. While it is preferred to align these with one accelerometer (e.g. accelerometer 12) substantially parallel to the sole 11 and the other 14 substantially perpendicular thereto this is not essential.

The tilt angle $\theta$ is the angle between a datum plane 100 which (FIG. 3a), as will be described below is defined by a surface 11 represented by the sole 11 of the foot or shoe 10. The sole 11 has a fixed orientation relative to the two accelerometers 12 and 14, i.e. the sole 11 of the shoe 10 defines a plane and the position of the sole 11 on the shoe 10 in the stance position of the gait defines the datum plane 100 for the next stride. The angle $\theta$ is the instantaneous angle between the plane defined by the sole 11 and the previously defined datum plane 100 for that particular stride (see FIG. 3a).

Figure 3A:
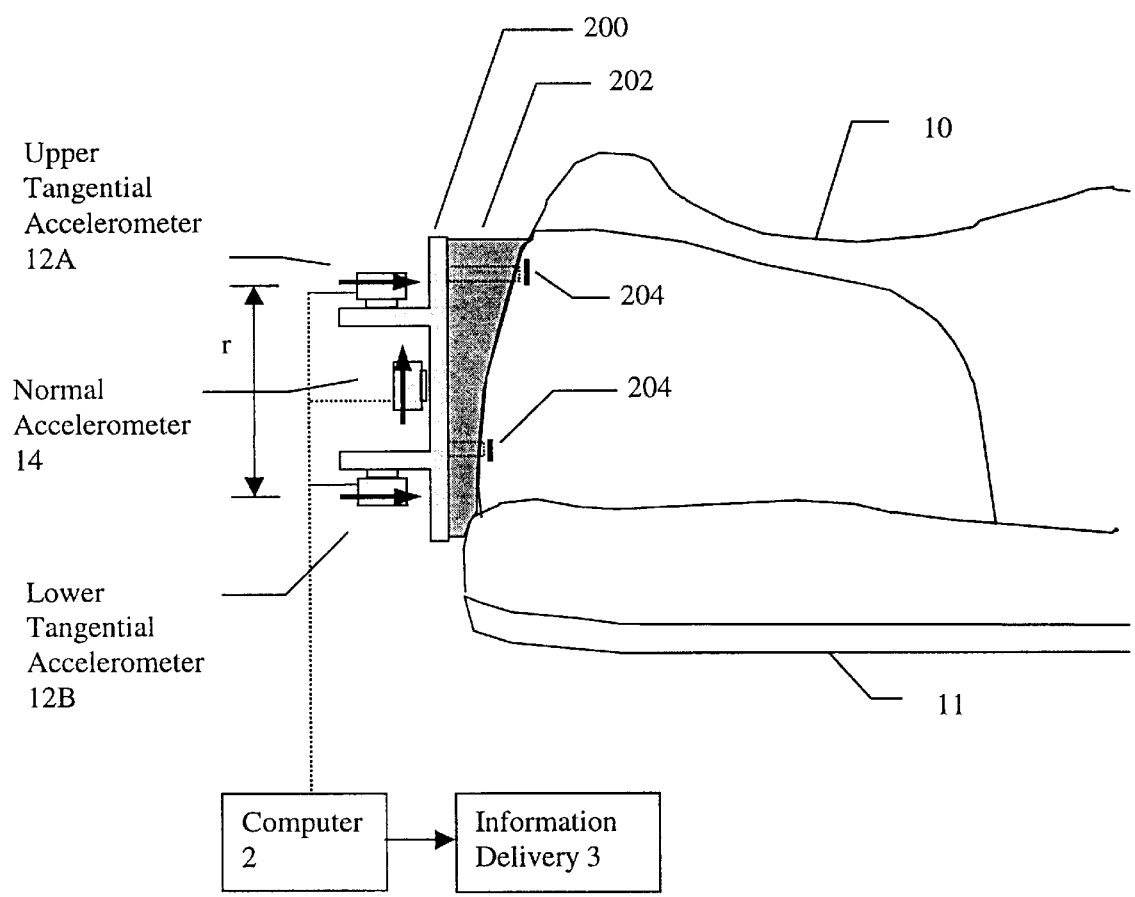
FIGS. 3a and 3b the various angles and movement vectors of the shoe.
Figure 3B:
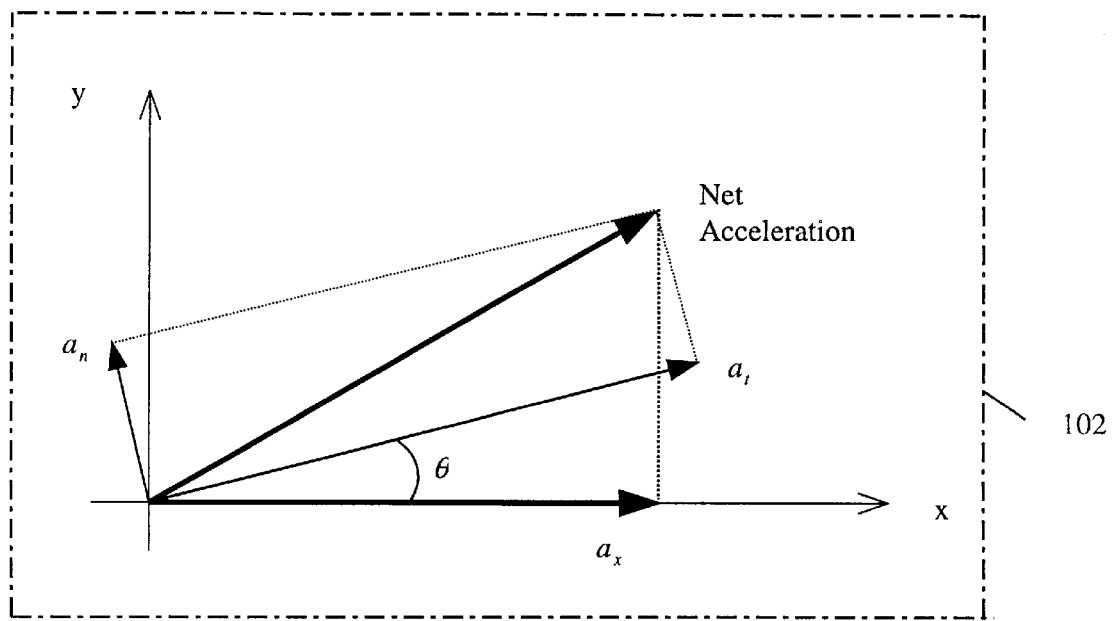

As the shoe 10 is tilted during the stride, the accelerometers 12 and 14 measure the accelerations $a_t$ and $a_n$ in their respective directions as depicted in FIG. 3a. Knowing the foot angle $\theta$ at any point in time, these accelerations may be resolved into their components in the selected direction, but normally are resolved to a direction substantially parallel to the direction of the plane 100 (referred to below as the horizontal direction as it will generally be approximately horizontal as it will generally be approximately horizontal) and then added together (with vectors) yielding the net acceleration in the horizontal direction (see FIG. 3b).

Since the accelerometers are mounted in the plane of motion 102 (see FIG. 3b) the net acceleration is also parallel to the plane of motion 102, i.e. the direction in which the stride is taken. This horizontal acceleration can be calculated by the following equation:

$$a_x = a_t \cos(\theta) - a_n \sin(\theta)$$

where $a_x$=acceleration in horizontal direction $a_t$=acceleration of tangential accelerometer 12

$a_n$=acceleration of normal accelerometer 14

$\theta$=angle of tilt of accelerometer 12 i.e. sole 11 of shoe 10 with respect to plane 100 which in normal operation will represent the ground or surface on which the stride is taking place.

Figures 4A, 4B, 4C:
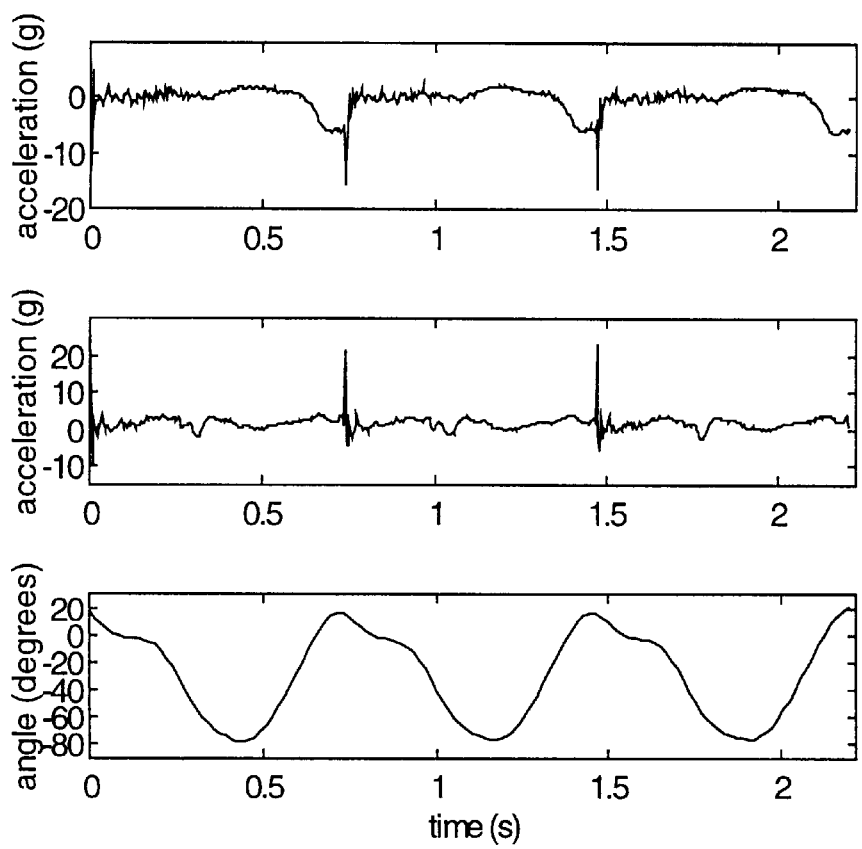
FIGS. 4a, 4b and 4c are graphs of tangential acceleration, normal acceleration and angle of tilt of the foot respectively versus time.

FIGS. 4a, b, c show typical data gathered over several gait cycles for the two mutually perpendicular accelerometers 12 and 14 and tilt sensor 16 versus time in second(s). This includes data collected by the tangential accelerometer (FIG. 4a), by the normal accelerometer 14 (FIG. 4b) and finally, FIG. 4c shows the angle of foot tilt through the gait cycles.

Figure 5A:
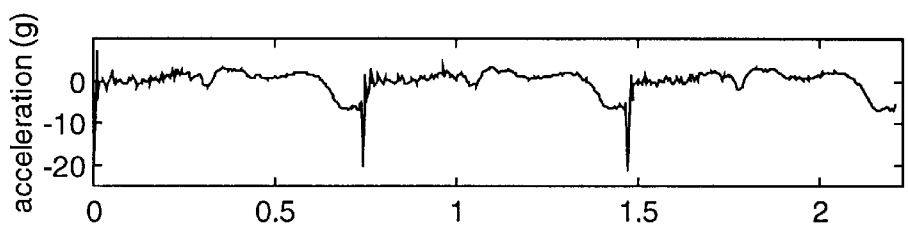
FIGS. 5a, 5b and 5c are plots of horizontal acceleration, foot velocity and speed of travel respectively versus time.
Figure 5B:
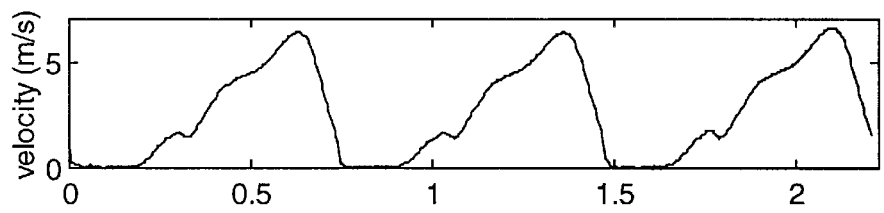
Figure 5C:
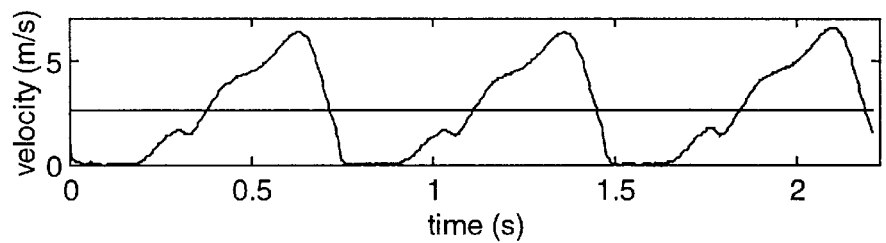

The net horizontal acceleration $a_x$, shown in FIG. 5a, is integrated to yield the foot velocity as a function of time (FIG. 5b). This velocity is averaged over several studies (three studies or cycles in this example) to yield the mean speed of travel shown as a straight line in FIG. 5c. The mean velocity of the walker/runner, over the given time interval, corresponds with the calculated mean horizontal foot velocity during the same time period.

Other gait parameters may also be easily derived from the measured data. These include, but are not limited to, stride rate, stride length, total distance traveled as well as angular velocities and accelerations.

Primary Components

As above described, the gait speedometer shown in FIG. 6 includes two linear accelerometers and an inclinometer or tilt sensor 16 all mounted on the ankle or shoe 10 in fixed relation to the datum plane defining surface or sole 11. The required characteristics of the accelerometers and inclinometer/tilt sensor will be described and specific prototype selections that have been tested or considered are listed below.

Accelerometers

The transducers are mounted on the foot or shoe. It is necessary that they must not interfere or influence natural gait; this requires that they are small and lightweight.

The device may be battery powered; this requires that the primary components and associated circuits possess low-power consumption characteristics.

Human gait is a very low frequency phenomenon; the accelerometers used in thus device must be able to measure down to these frequencies.

The accelerometer transducer cluster is mounted on the foot or shoe and will thus be subjected to large impact forces and abuse. It is necessary that the accelerometers be rugged and durable to be able to survive in this environment.

The linearity, repeatability and noise levels must be such that the accuracy of measurement is acceptable for the application.

The accelerometers used in the development work of this invention are manufactured by Analog Devices (part no.'s ADXL50 and ADXL150/250). These accelerometers make use of micro-machining techniques to build the transducer into a silicon chip. This accounts for the small size, low power consumption and accuracy of the devices.

The invention described herein is not limited to the above mentioned accelerometer family. Other micro-machined accelerometers are currently produced or are under development by different manufacturers and could be considered for this purpose. As well, more conventional accelerometer technologies are candidates for this invention including strain-gauge and piezo-electric types.

Inclinometers/Tilt Sensors

The transducer is mounted on the foot or shoe. It is necessary that it must not interfere or influence natural gait; this requires that it be small and lightweight.

The device may be battery powered; this requires that the primary components and associated circuits possess low-power consumption characteristics.

The transducer cluster is mounted on the foot or shoe and will thus be subjected to large impact forces and abuse. It is necessary that the angle measurement device be rugged and durable to be able to survive in this environment.

The linearity, repeatability and noise levels must be such that the accuracy of measurement is acceptable for the application.

To be able to determine the foot angle, many approaches are possible. It is possible to measure the foot angle directly by means of a tilt sensor or other suitable device. It is possible to measure the foot's angular velocity by means of a rate gyro or other suitable device and then integrate the signal once to determine the foot angle. It is possible to measure the foot's angular acceleration by means of an angular rotation accelerometer or other suitable device and then integrate the signal twice to determine the foot angle.

Signal processing a pair of spaced parallel accelerometers to extract tilt information from the foot's angular acceleration, will be described in more detail herein below as it is the preferred system for determining the angle θ.

Signal Conditioning

Figure 7:
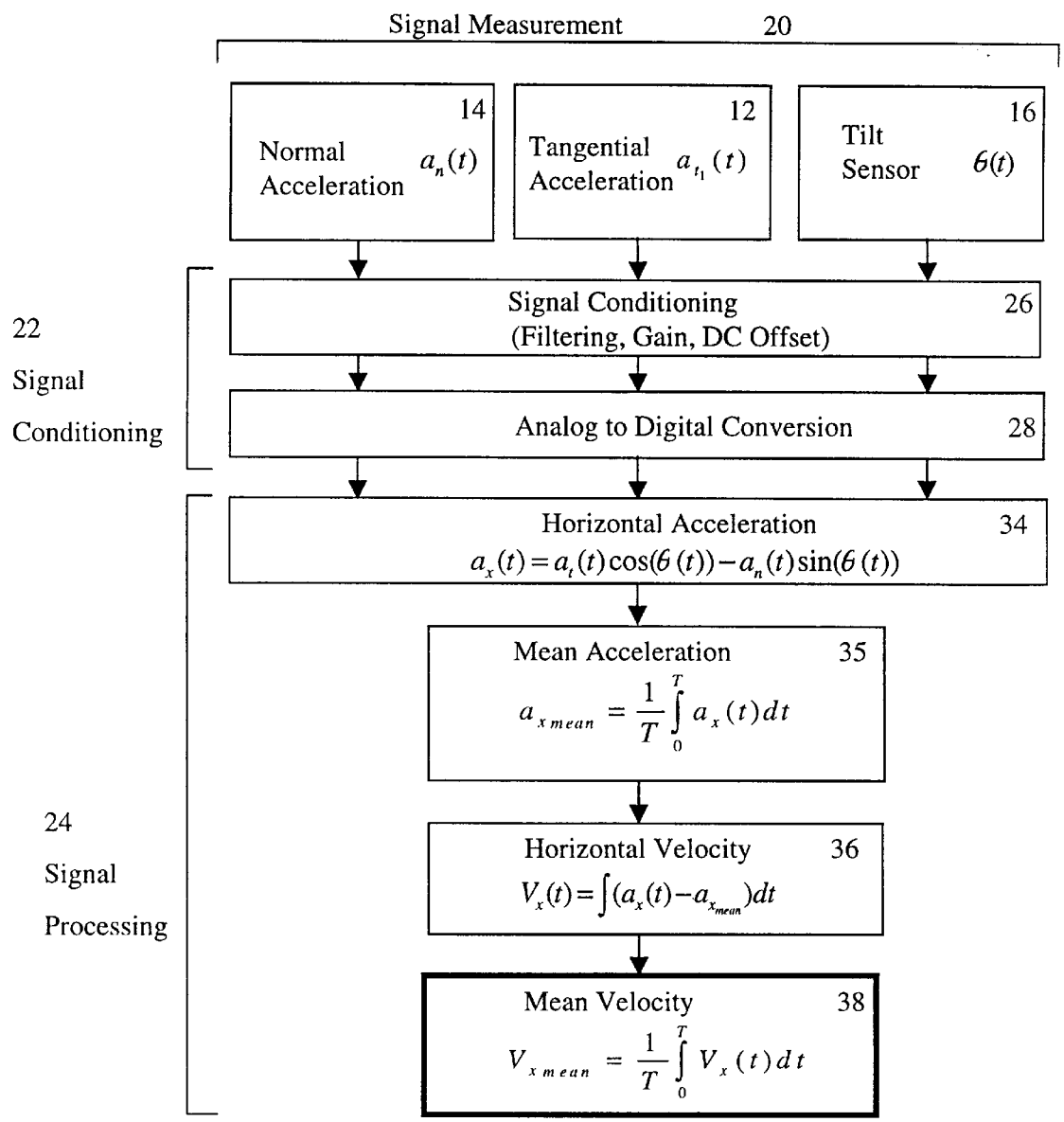
FIG. 7 is a flow diagram of one mode of operation of the computer.

Full implementation of the gait speedometer includes signal measurement 20, signal conditioning 22 which includes processing components such as amplifiers, filters and signal processing 24. A signal path or flow diagram shown in FIG. 7 outlines the process. Signals emerge from the three primary transducers (normal and tangential accelerometers and inclinometer) and pass through signal conditions 22 which includes signal conditioning 26, by applying zero adjustments, gains, filters, etc. and analog to digital conversion 28. These signals from the accelerometers 12 and 14 are then combined using the angle θ to determine the net horizontal acceleration 34 from which the instantaneous foot velocity i.e. horizontal velocity 36 and mean velocity 38 may be determined.

Gait Parameter Calculation and Display

Once the instantaneous foot velocity has been determined 36, it may if desired be transmitted via a wireless transmitter/receiver pair 5, 6 or signal wires 4 to a calculation/display unit 3 (such as a wristwatch sized device, portable calculation device or desktop computer) to store and display various velocity parameters along with many other gait indicators (see FIG. 6).

More Preferred Embodiment

A second embodiment of the invention is shown and will be described with reference to FIGS. 1A to 16A inclusive. Like reference numerals are used to indicate like parts in all embodiments.

Figure 1A:
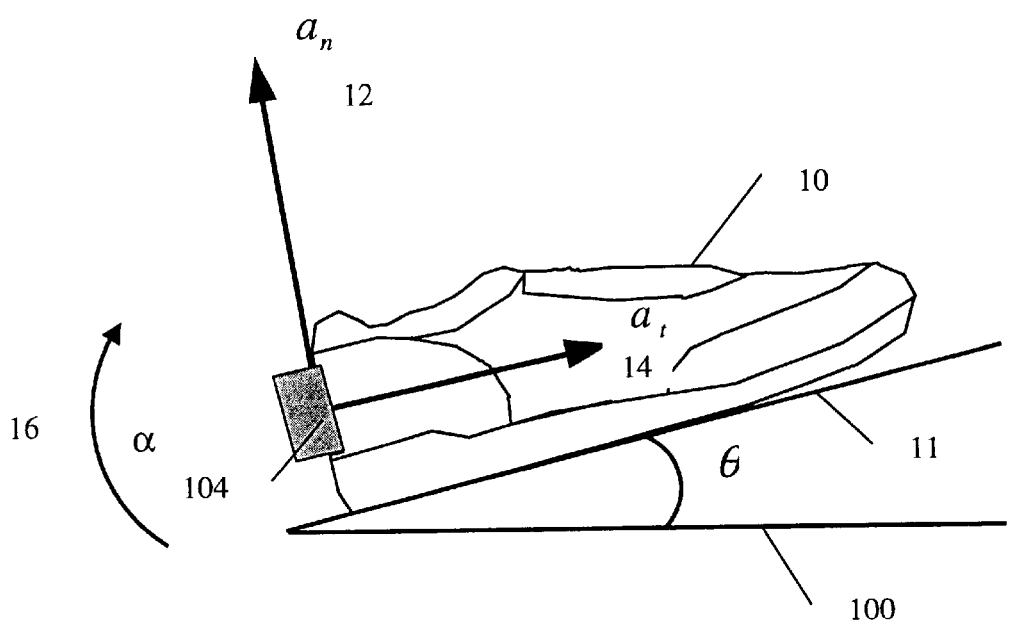
FIG. 1A shows the relationship of the normal, tangential and angular acceleration vectors and the shoe angle.
Figure 2A:
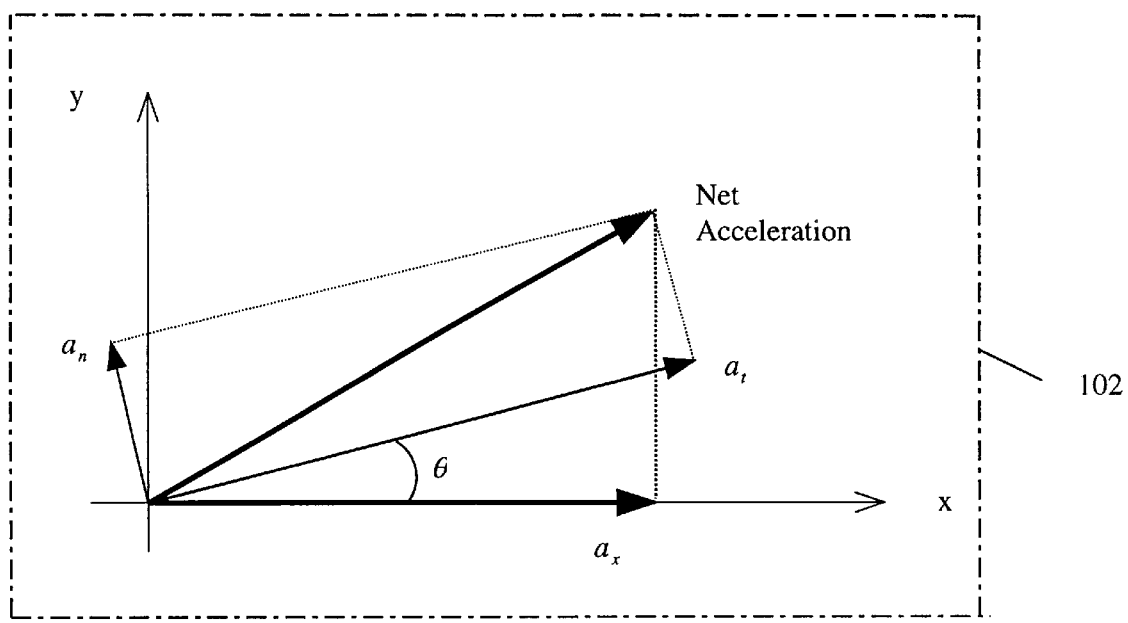
FIG. 2A shows how the vectors combine to produce the net acceleration vector.

Accelerometers are placed on the foot in essentially the same manner as described above so that normal accelerations, $a_n$, tangential accelerations, $a_t$, and angular accelerations, α, preferably about the intersection 104 of the tangential and normal acceleration vectors $a_t$ and $a_n$ respectively can be simultaneously measured (see FIG. 1A). The normal accelerometer measures 14 acceleration perpendicular to the base or sole 11 of the foot or shoe 10 which as above described provides the datum plane 100 defining surface 11 that defines the datum plane 100 for each stride when the sole 11 is at rest in the stance phase A of each stride. The tangential accelerometer 12 is sensitive to accelerations parallel to the base or sole 11 of the foot or shoe 10. The absolute direction of these accelerations vary continuously as the foot moves through a gait cycle. The measured angular acceleration is integrated twice to yield the foot angle θ. This angle θ is then used to resolve the normal and tangential accelerations into a net horizontal acceleration as shown in FIG. 2A. The horizontal acceleration is then integrated to find the velocity of the foot as a function of time. The subject's mean speed of travel is determined by averaging the foot velocity over an integer number of foot strides.

The term horizontal or net horizontal acceleration velocity etc. is used for convenience as though the vector is horizontal i.e. parallel with a horizontal datum plane 100. This vector will normally be parallel to the datum plane 100 and the plane of motion 104. It also will be apparent that these vectors may be resolved into any selected plane or direction i.e. horizontal, vertical or somewhere in between.

It was chosen to place accelerometers on the foot because the foot follows a regular pattern of acceleration and deceleration as the foot travels through the air and comes to rest on the ground for each stride as indicated by the segments A, B, C and D of the stride in FIG. 1. The small stationary period of time when the foot rests on the ground provides a useful point of reference for each stride and is used to define the datum plane 100 for each stride. With this method, each stride is independently measured and thus there is no accumulating error if the measurement were interconnected. It makes no assumptions regarding stride length, gait type (walking, jogging or running) and it accounts for the flight phase of a running gait.

Three accelerometers (two tangential 12A and 12B and a normal 14) are mounted on a small aluminum bracket 200 fastened via a leveling wing 202 by two screws 204 to the heel counter of a shoe 10 as shown in FIG. 3A. The upper and lower accelerometers 12A and 12B provide a pair of spaced substantially parallel accelerometers that measure tangential accelerations, while the middle normal accelerometer 14 measures the normal acceleration. The angular acceleration is determined by taking the difference of the accelerations generated by the upper and lower accelerometers divided by the distance between them (shown in FIG. 3A by the distance r). It is preferred that these accelerometers 12A and 12B be equally spaced from accelerometer 14, but this is not essential. The net tangential acceleration of the heel preferably is taken as the average of the upper and lower tangential accelerometers. This data is delivered to a computer 2 that then determines the acceleration, velocity and other information which may be delivered to the user, for example, by audio or visual means such as an earphone or digital or analogue visual display or any other suitable means schematically indicated at 3.

Suitable accelerometers are those made by Analog Devices (type ADXL50AH). The accelerometers were connected by shielded cables to a signal conditioning unit 26 which provided gain, zero offset adjustment, and anti-alias filtering etc. and then connected from an analog to a digital signal in converter 28 (see FIG. 15A).

Signal Processing and Analysis

Typical normal and tangential accelerations for strides (4 in this example) of a subject jogging at 3 m/s (7 mph) are shown in FIG. 4A. A close-up of a tangential signal from the first stride shown in FIG. 4A is shown in FIG. 5A. The initial sharp spike corresponds to heel strike. The flatter section of the signal in the segment immediately following impact, is the stance phase of the gait. The negative dip in the acceleration just after toe-off corresponds to the heel being raised as the knee flexes. The positive acceleration during the middle portion of the swing phase corresponds to the foot accelerating forward. During the latter portion of the swing phase, as the foot is slowed down in preparation for contact with the ground, there is a period of negative acceleration.

Stride beginning and ending locations were found from the impact spikes when the subject's foot struck the ground. An algorithm based on finding a local maximum after the acceleration crosses a variable threshold value was used to find the impact spikes. The heel decelerates to a low speed before striking the ground but does not actually reach zero velocity until just slightly after impact. A location of approximately 0.1 seconds after heel strike was chosen to denote the beginning of a stride since this is approximately where the foot velocity is zero. This position is used to determine the datum plane 100 which corresponds with the plane of the sole 11 at this point in time.

Foot Angle

It is preferred to measure angular acceleration and then integrate twice to determine the foot angle θ. The measurement of the angular acceleration is accomplished by taking the difference between two parallel tangential accelerometers 12A and 12B.

After dividing the sequence into strides, the foot's angular position is determined. Coordinates are chosen so that the tilt is considered zero when the foot is in the zero velocity position i.e. the stance phase of the gait selected at 0.1 seconds after the heel strike i.e. a 0.1 second offset, and positive when the toe was pointed upwards as shown in FIG. 1A. The foot's angular acceleration is found by subtracting the upper tangential acceleration, $a_{t_1}$, from the lower tangential acceleration, $a_{t_2}$. The angular acceleration in radians/sec², α, is calculated by dividing by the distance between the two accelerometers as indicated at 300 in FIG. 15A.

$$\alpha = \frac{(a_{t_2} - a_{t_1})}{r}$$

The resulting angular acceleration, from the data shown in FIG. 4A, is shown in FIG. 6Aa. This data was then integrated using an accumulating sum and the resulting angular velocity, ω (in radians/sec) is shown in FIG. 6Ab. This result was once again integrated to produce the foot angle, θ, shown in FIG. 6Ac. Note how the very noisy and nondescript appearing signal in FIG. 6Aa is transformed into a very regular, smoothed function in FIG. 6Ac. Low frequency drift is evident in the foot angle signal.

Figure 15A:
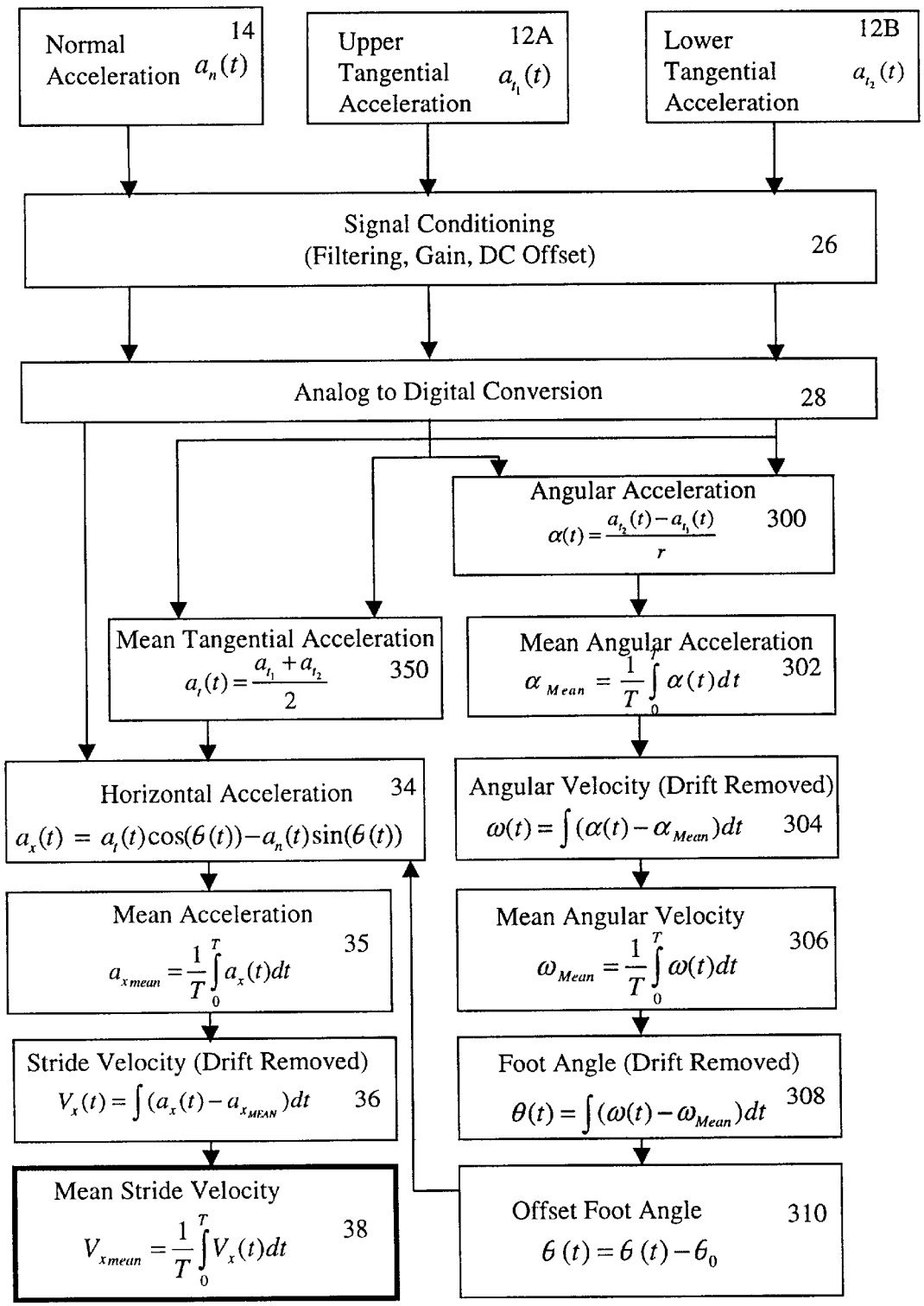
FIG. 15A is a flow diagram similar to that shown in FIG. 7.

A preferred method to convert drift is to first determine the mean angular acceleration $\alpha_{mean}$ as indicated at 302 and to remove zero offset drift from α and ω by subtracting each signal's mean for each individual stride before integrating as indicated at 304 in FIG. 15A to define angular velocity ω.

The mean angular velocity $\omega_{mean}$ is determined as indicated at 306 in FIG. 15A and then used to compute the angle θ as indicated at 308 and the position of the datum plane 100 using the offset $\theta_O$(0.1 seconds) described above as indicated at 310.

Figure 7A:
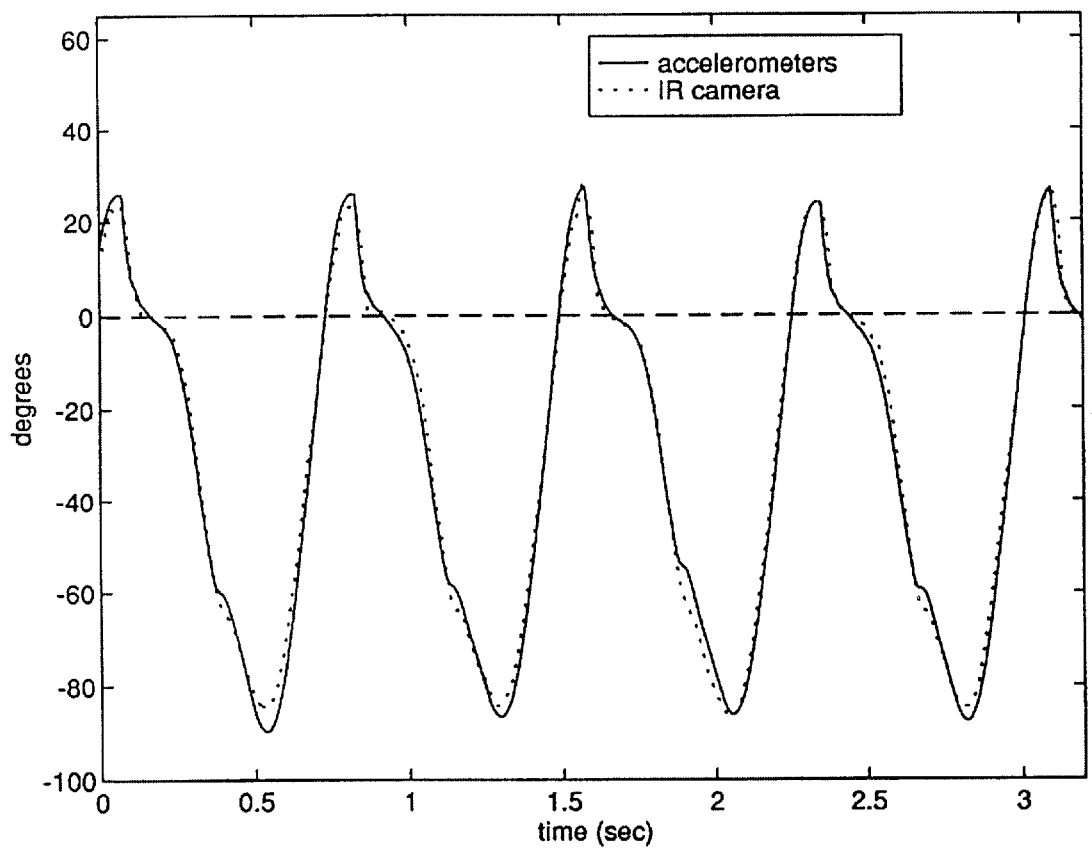
FIG. 7A illustrates the accuracy of determined foot angle over time.

FIG. 7A shows the foot angle θ that results from the zeroing and integrating method on the data from FIG. 6Aa (the zeroing and integrating is applied twice; once in the conversion of α to ω and once again in going from ω to θ). It is seen that it compares well with the independent θ from the infrared camera system that was used to film the subject.

Foot Velocity

Components of the tangential and normal acceleration are combined using the foot tilt angle θ to find the horizontal acceleration, $a_x$.

$$a_x = \frac{(a_{t_1} + a_{t_2})}{2} \cos(\theta) - a_n \sin(\theta)$$

Figure 8A:
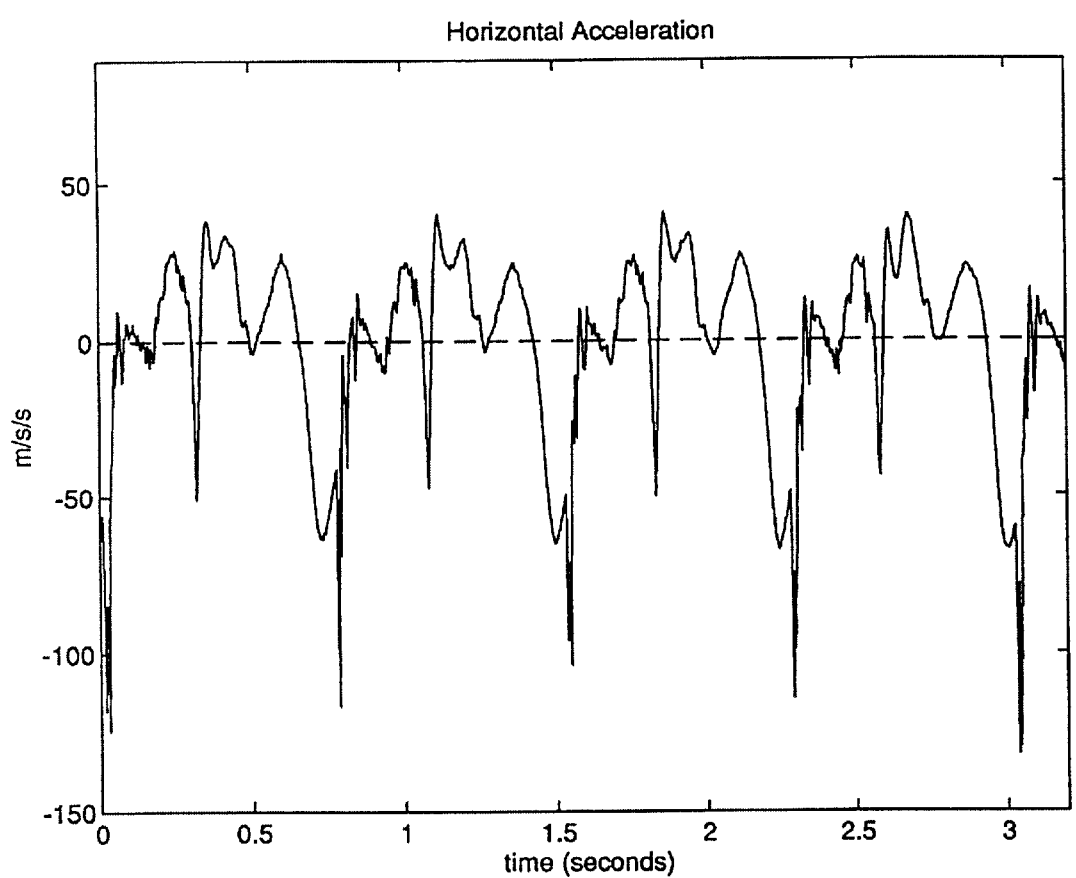
FIG. 8A is a plot of horizontal acceleration versus time.
Figure 9A:
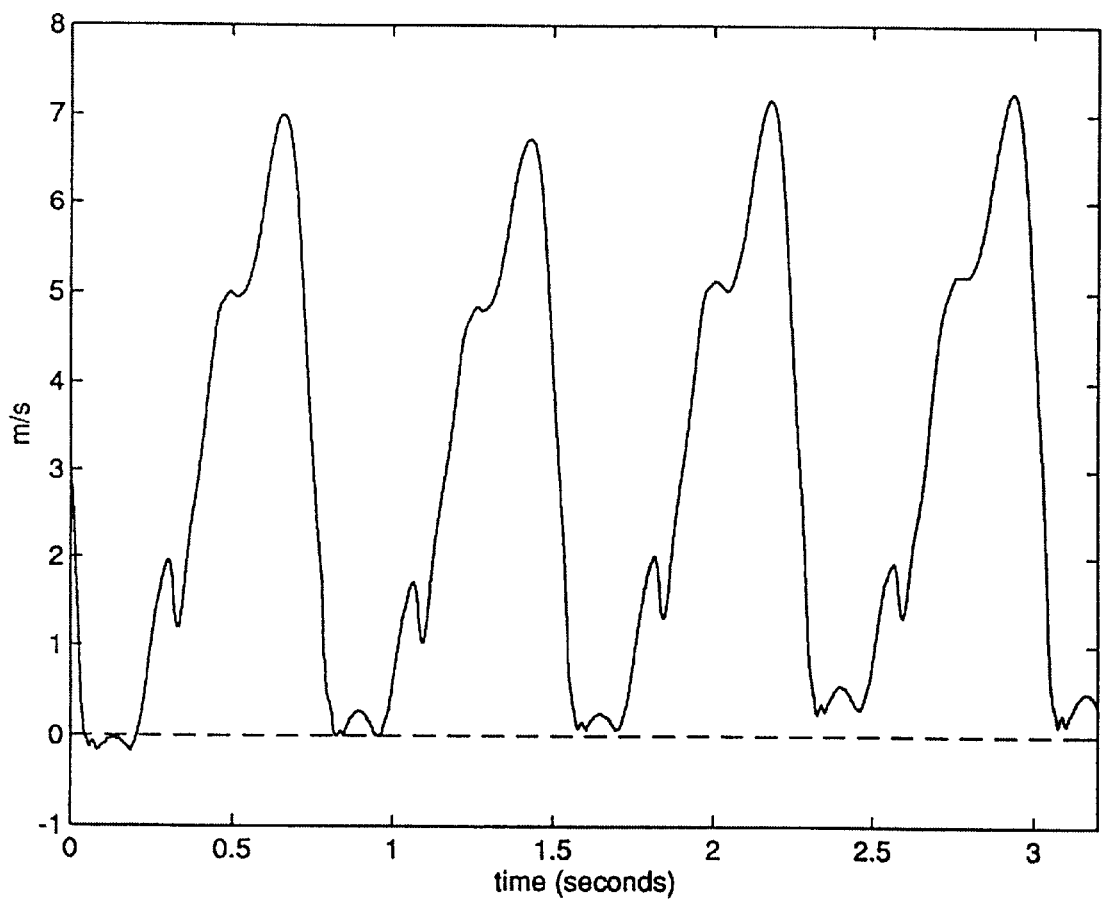
FIG. 9A is a plot of drifting velocity versus time.
Figure 10A:
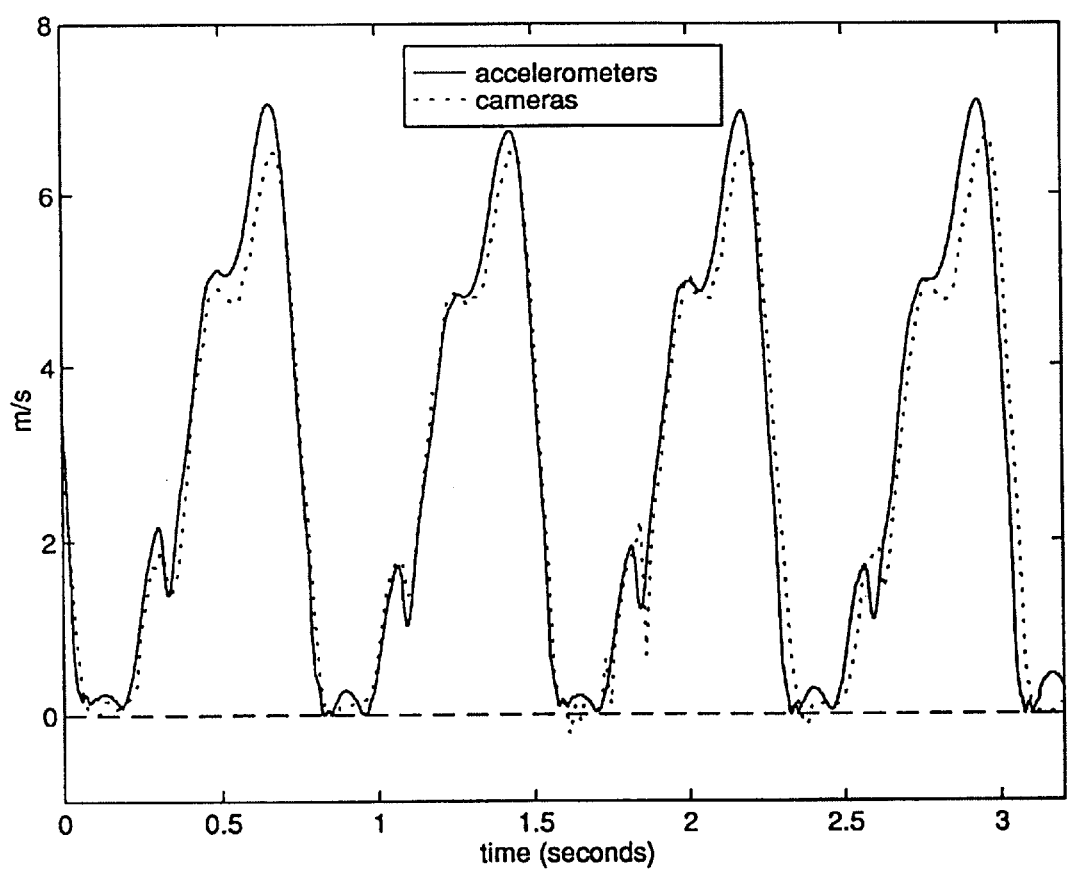
FIG. 10A is a plot of foot velocity versus time.

From the measured acceleration data in FIG. 4A and the calculated foot angle shown in FIG. 7A, the resulting horizontal acceleration is shown in FIG. 8A. An integration of $a_x$ yields velocity $v_x$ parallel to plane 100 (or with appropriate changes any other selected direction) as a function of time, as shown in FIG. 9A. It is seen that this signal also has low frequency drift. To correct the drift, zero offset was removed from the net horizontal acceleration since the horizontal velocity is zero at the beginning and end of each cycle. FIG. 10A compares the velocities computed from the camera system and the velocities from using the zeroing and integrating algorithm on the acceleration data. Excellent agreement is seen in the form of the two curves. The final mean velocities agree to within a few percent.

A further improvement in results is usually achieved by using the assumption that the minimum foot velocity is zero. This suggests that if any part of the entire velocity curve dips below zero there has been some small error somewhere. If the error has not corrupted the shape of the curve, it can be corrected by simply shifting the entire curve up so that the new minimum is exactly zero.

Generally, when two parallel accelerometers are used to determine α, it is preferred to use the average of these two measurements to determine the mean, in this example the mean tangential acceleration, as indicated at 350 and generate a mean velocity as indicated by steps 34, 35, 36, and 38 described above and also shown in FIG. 15A.

Results Using the Preferred Version

Figure 11A:
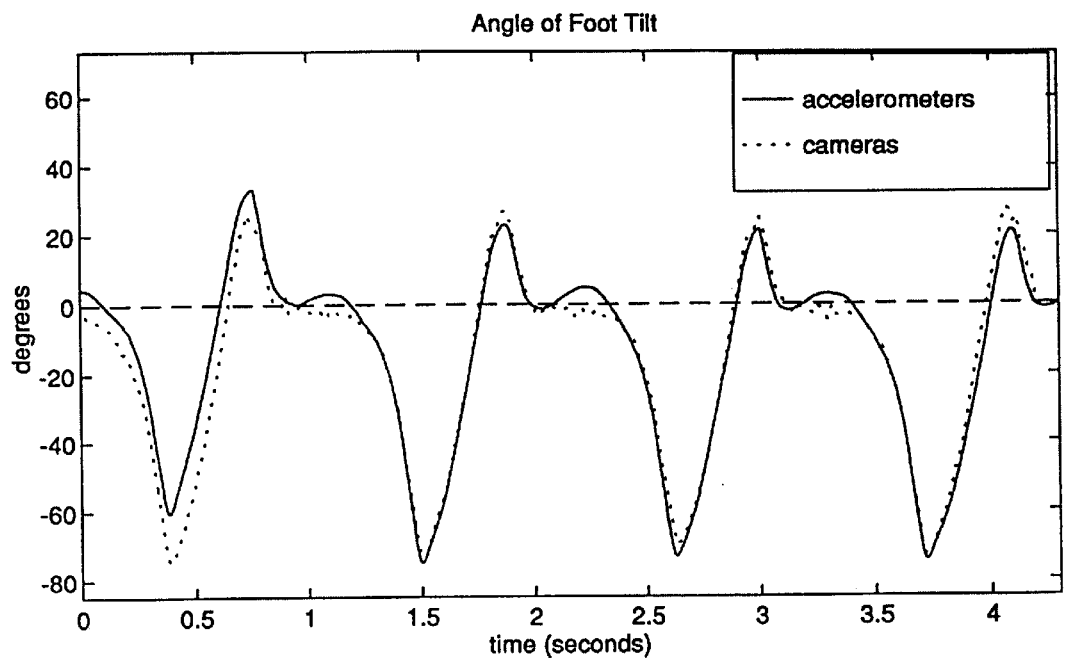
FIGS. 11A and 13A are plots of angle of foot tilt versus time.
Figure 12A:
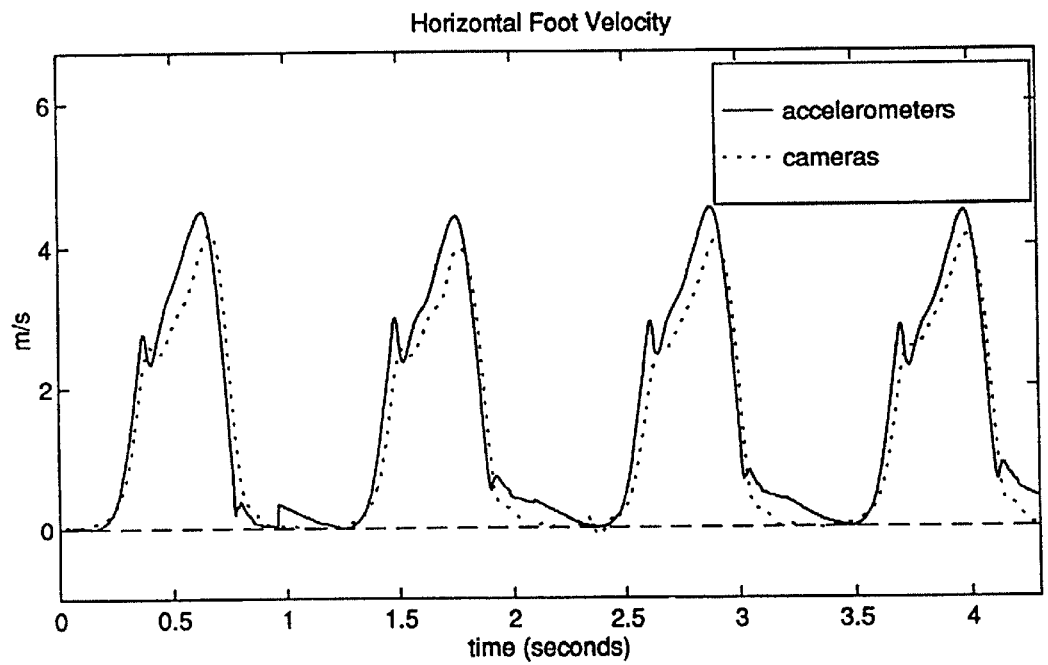
FIGS. 12A and 14A are plots of horizontal foot velocity versus time.
Figure 13A:
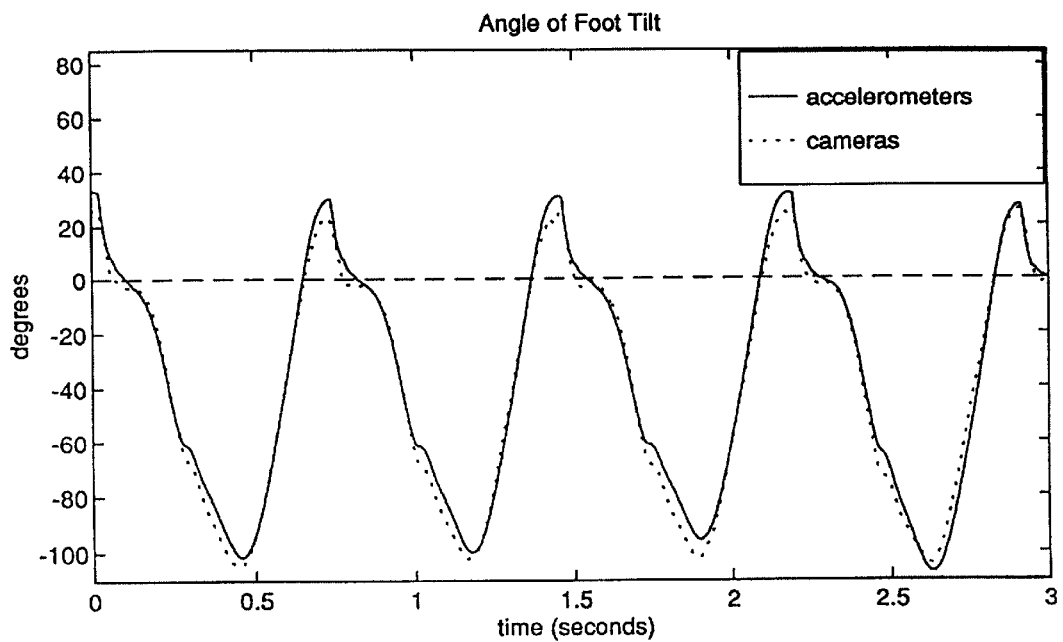
Figure 14A:
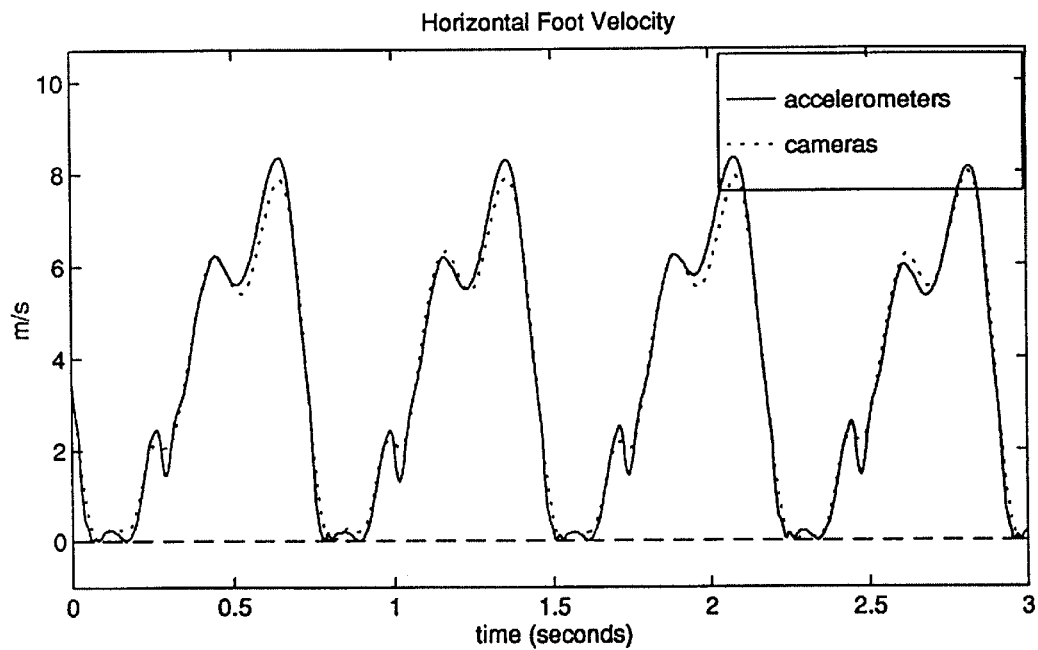

For the sake of coherence, all of the figures that have been shown so far have been of the same trial, a 3 m/s jog. FIGS. 11A and 12A show the critical parameters, namely the foot angle, θ, and foot velocity, $v_x$, for a 1.3 m/s walk, while FIGS. 13A and 14A show the same for a 3.8 m/s run respectively. In these figures, the calculated values from the method described herein are compared to video camera analysis of the same parameters. It is observed that there is excellent overall agreement between the foot angle and foot velocity for these cases.

Figure 16A:
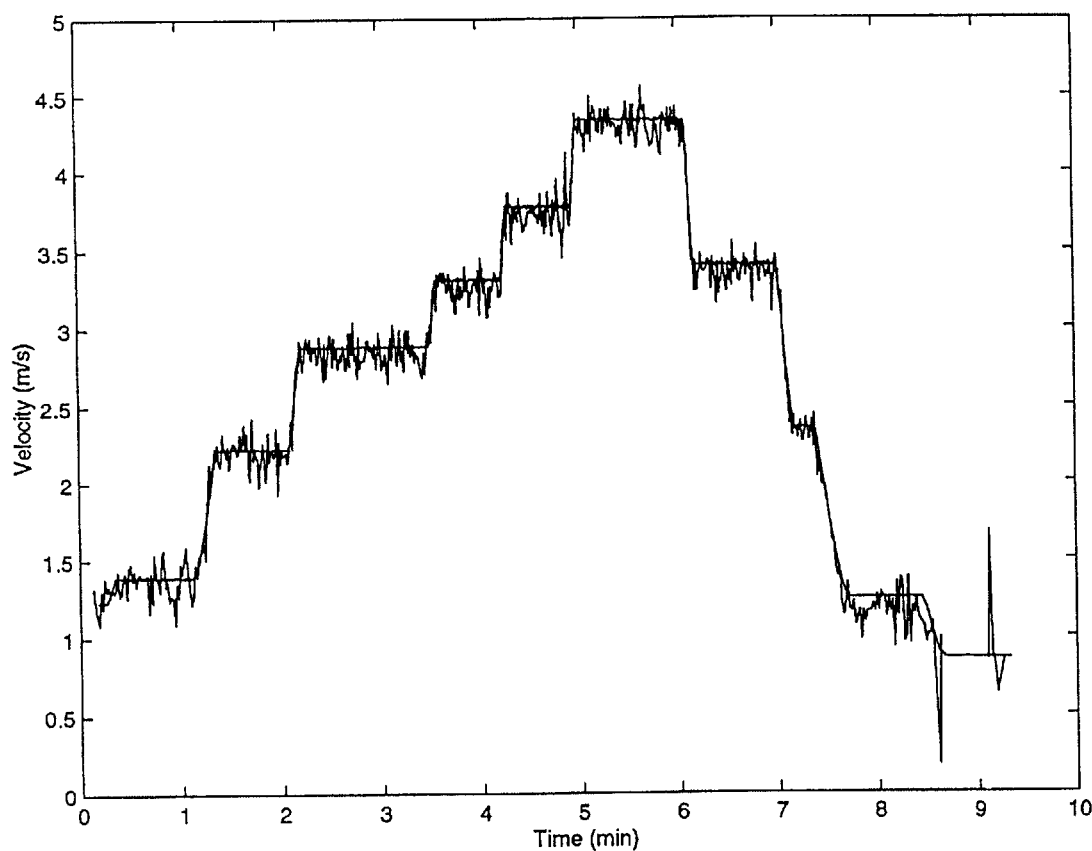
FIG. 16A is a plot of velocity versus time showing correlation of the invention at different stride velocities.

FIG. 16A shows a controlled experiment where the speed of a treadmill was selectively increased and the jogging speed of the runner measured using the present invention. The stopped line shows treadmill speed while the other plot is the results using the present invention. It is apparent that the results obtained using the present invention correlate very well with the actual speeds of the treadmill.

Final Notes

It will be apparent that the invention may be used for many applications other than those described above including general kinematic measurements in one, two or three dimensions depending on the number and position of the accelerometers and angle measurement devices. Thus the invention may be used in robotic controls, linkage and trajectory analysis, for example. Clearly, the invention finds specific application in the biomedical field in prosthetics and as gait speedometers for walkers, runners or other athletes. Note that the use of this device is not limited to human applications.

A primary advantage of the described invention, is that all calculated gait parameters are available as function of time. This opens up a wide range of real-time post-processing possibilities for use in scientific analysis and control operations.

While the disclosure has described the accelerometers, etc. mounted on the counter of the shoe 10 they may be mounted at any appropriate location in fixed relation to the datum plane defining surface 11 or other such means. For example, they could be mounted to the shoe laces or pinned to the side of the shoe or built into the sole of the shoe.

Having described the invention, modifications will be evident to those skilled in the art without departing from the spirit of the invention as described above.

I claim:

1. A method of determining gait kinematics in each of a plurality of strides comprising during each said stride defining a fresh datum plane, determining angles between a pair of mutually perpendicular accelerometers to said datum plane, said pair of mutually perpendicular accelerometers adapted to measure acceleration in two mutually perpendicular directions in a plane of motion substantially perpendicular to said datum plane, measuring acceleration in said plane of motion in said two directions and converting said accelerations to provide acceleration in a selected direction for each said stride.

2. A method as defined in claim 1 wherein said selected direction is parallel to the datum plane and said plane of motion.

3. A method as defined in claim 2 further comprising integrating said acceleration in said selected direction to define velocity in said selected direction.

4. A method as defined in claim 1 wherein said datum plane is defined by orientation of a sole plane when said sole plane is at rest on a surface in a stance phase of said gait and wherein said pair of mutually perpendicular accelerometers are positioned in fixed relationship to said sole plane.

5. A method as defined in claim 2 wherein said datum plane is defined by orientation of a sole plane when said sole plane is at rest on a surface in a stance phase of said gait and wherein said pair of mutually perpendicular accelerometers are positioned in fixed relationship to said sole plane.

6. A method as defined in claim 3 wherein said datum plane is defined by orientation of a sole plane when said sole plane is at rest on a surface in a stance phase of said gait and wherein said pair of mutually perpendicular accelerometers are positioned in fixed relationship to said sole plane.

7. A method as defined in claim 1 wherein said datum plane is defined by orientation of a sole plane when said sole plane is at rest on a surface in a stance phase of said gait and wherein said determining angles of a pair of mutually perpendicular accelerometers is based on measurements of a pair spaced parallel accelerometers positioned at a selected angle to said sole plane.

8. A method as defined in claim 2 wherein said datum plane is defined by orientation of a sole plane when said sole plane is at rest on a surface in a stance phase of said gait and wherein said determining angles of a pair of mutually perpendicular accelerometers is based on measurements of a pair spaced parallel accelerometers positioned at a selected angle to said sole plane.

9. A method as defined in claim 3 wherein said datum plane is defined by orientation of a sole plane when said sole plane is at rest on a surface in a stance phase of said gait and wherein said determining angles of a pair of mutually perpendicular accelerometers is based on measurements of a pair spaced parallel accelerometers positioned at a selected angle to said sole plane.

10. A method as defined in claim 4 wherein said datum plane is defined by orientation of a sole plane when said sole plane is at rest on a in surface a stance phase of said gait and wherein said determining angles of a pair of mutually perpendicular accelerometers is based on measurements of a pair spaced parallel accelerometers positioned at a selected angle to said sole plane.

11. A method as defined in claim 5 wherein said datum plane is defined by orientation of a sole plane when said sole plane is at rest on a surface in a stance phase of said gait and wherein said determining angles of a pair of mutually perpendicular accelerometers is based on measurements of a pair spaced parallel accelerometers positioned at a selected angle to said sole plane.

12. A method as defined in claim 6 wherein said datum plane is defined by orientation of a sole plane when said sole plane is at rest on a surface in a stance phase of said gait and wherein said determining angles of a pair of mutually perpendicular accelerometers is based on measurements of a pair spaced parallel accelerometers positioned at a selected angle to said sole plane.

13. A method as defined in claim 12 further comprising integrating said velocity to define distance in said selected direction.

14. A method as defined in claim 12 further comprising averaging said velocity over a plurality of strides to provide average velocity.

15. A device for measuring stride kinematics comprising means for mounting a pair of mutually perpendicular accelerometers in fixed relationship to a datum plane defining surface and adapted to measure acceleration in two mutually perpendicular directions, means defining a datum plane for each stride for which said stride kinematics is measured as a plane occupied by said datum plane defining surface when said datum plane defining surface is in a stationary position in a stance phase of each said stride for which said stride kinematics is being measured, means for determining angular orientation of said accelerometers to said datum plane, and means for determining acceleration in a selected direction based on measurements of acceleration by said mutually perpendicular accelerometers and said determined angular orientation of said accelerometers to said datum plane in each said stride.

16. A device as defined in claim 15 wherein said means for determining angular orientation of said accelerometers to said datum plane for each said stride comprises of a pair of spaced substantially parallel accelerometers mounted in fixed relationship to said datum plane defining surface and means for calculating angular orientation based on differences in accelerations measured by said pair of spaced substantially parallel accelerometers in each said stride.

17. A device as defined in claim 15 further comprising means for converting acceleration in said selected direction to velocity in said selected direction.

18. A device as defined in claim 16 further comprising means for converting acceleration in said selected direction to velocity in said selected direction.

19. A device as defined in claim 17 further comprising means to convert said acceleration in said selected direction to distance in said selected direction.

20. A device as defined in claim 18 further comprising means to convert said acceleration in said selected direction to distance in said selected direction.

* * * * *